(12) United States Patent
Cook et al.

(10) Patent No.: US 9,707,105 B2
(45) Date of Patent: Jul. 18, 2017

(54) MAGNETIC PROSTHETIC IMPLANTS AND METHODS THEREOF

(75) Inventors: Stephen D. Cook, New Orleans, LA (US); Shoib Bajaj, Kenner, LA (US); Laura P. Patron, Belle Chasse, LA (US); Peter Strzepa, Austin, TX (US)

(73) Assignee: Fellowship of Orthopaedic Researchers, Inc., Metairie, LA (US)

( * ) Notice: Subject to any disclaimer, the term of this patent is extended or adjusted under 35 U.S.C. 154(b) by 174 days.

(21) Appl. No.: 13/540,493

(22) Filed: Jul. 2, 2012

(65) Prior Publication Data

US 2013/0006356 A1    Jan. 3, 2013

Related U.S. Application Data

(60) Provisional application No. 61/503,571, filed on Jun. 30, 2011.

(51) Int. Cl.
*A61F 2/60* (2006.01)
*A61F 2/78* (2006.01)
*A61F 2/50* (2006.01)

(52) U.S. Cl.
CPC .......... *A61F 2/78* (2013.01); *A61F 2002/502* (2013.01); *A61F 2002/7887* (2013.01)

(58) Field of Classification Search
CPC ........ A61F 2002/7635; A61F 2002/764; A61F 2/60; A61F 2/6607; A61F 2/80; A61F 2002/5033; A61F 2/64; A61F 2002/6614; A61F 2/583; A61F 2/605; A61F 2/66; A61F 2/582
USPC ................. 623/24–65; 403/DIG. 1
See application file for complete search history.

(56) References Cited

U.S. PATENT DOCUMENTS

| 5,507,835 A * | 4/1996 | Jore ............................... 623/36 |
| 7,922,773 B1 | 4/2011 | Kuiken |
| 2005/0261783 A1 * | 11/2005 | Geilman ................... A61F 2/60 623/52 |

(Continued)

FOREIGN PATENT DOCUMENTS

EP        1743602 A1    1/2007

OTHER PUBLICATIONS

Patent Cooperation Treaty, PCT International Search Report, Issued in Connection with International Application No. PCT/US2012/045316; Oct. 11, 2012; 6 pages; Europe.

(Continued)

*Primary Examiner* — Ann Schillinger
(74) *Attorney, Agent, or Firm* — Haug Partners LLP

(57) ABSTRACT

Prosthetic implant devices and related methods are provided. The prosthetic implant devices includes an internal component and an external component. The internal component has an implant portion associated with one or more rare earth magnets. The internal component being of a size and shape suitable for surgical implantation into the residual limb of the amputee. The implant portion being of a size and shape suitable for surgical implantation into a bone within the residual limb of the amputee. The one or more rare earth magnets generating at least one magnetic field. The external component having a prosthetic connection associated with a magnetic element. The magnet element being in adaptable magnetic association with the at least one magnetic field generated by the one or more rare earth magnets.

7 Claims, 9 Drawing Sheets

(56) References Cited

U.S. PATENT DOCUMENTS

| | | |
|---|---|---|
| 2006/0293762 A1 | 12/2006 | Schulman et al. |
| 2009/0112207 A1 | 4/2009 | Walker et al. |
| 2009/0112262 A1 | 4/2009 | Pool et al. |
| 2009/0112263 A1* | 4/2009 | Pool et al. ............... 606/246 |
| 2009/0254196 A1* | 10/2009 | Cox ............... A61F 2/2814 |
| | | 623/33 |
| 2011/0224805 A1 | 9/2011 | Schulman et al. |
| 2012/0157996 A1 | 6/2012 | Walker et al. |

OTHER PUBLICATIONS

Patent Cooperation Treaty, PCT Written Opinion of the International Searching Authority, Issued in Connection with International Application No. PCT/US2012/045316; Oct. 11, 2012; 7 pages; Europe.

* cited by examiner

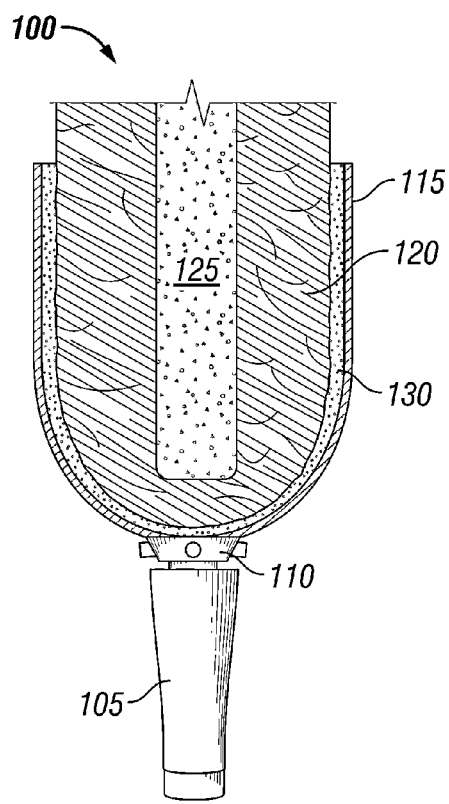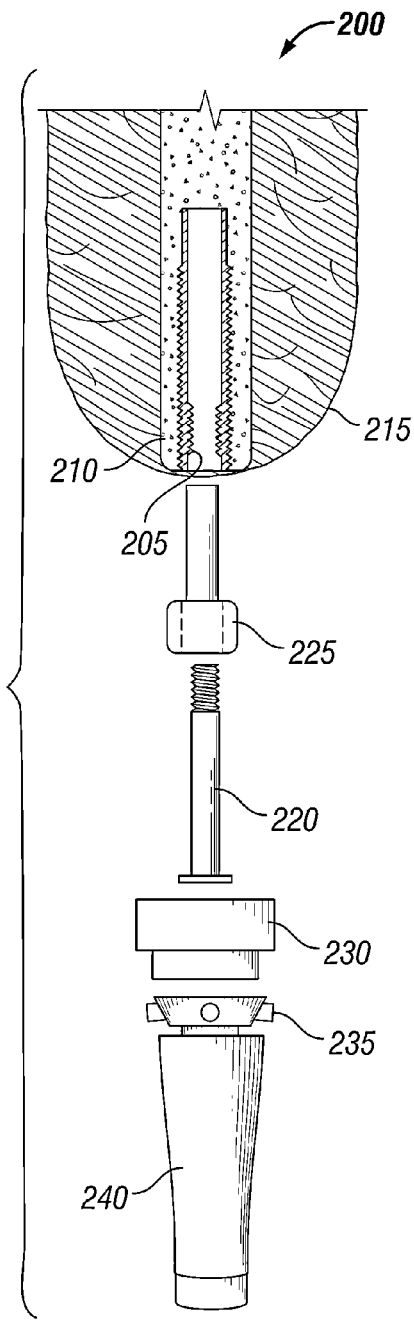
FIG. 1
(Prior Art)
FIG. 2
(Prior Art)

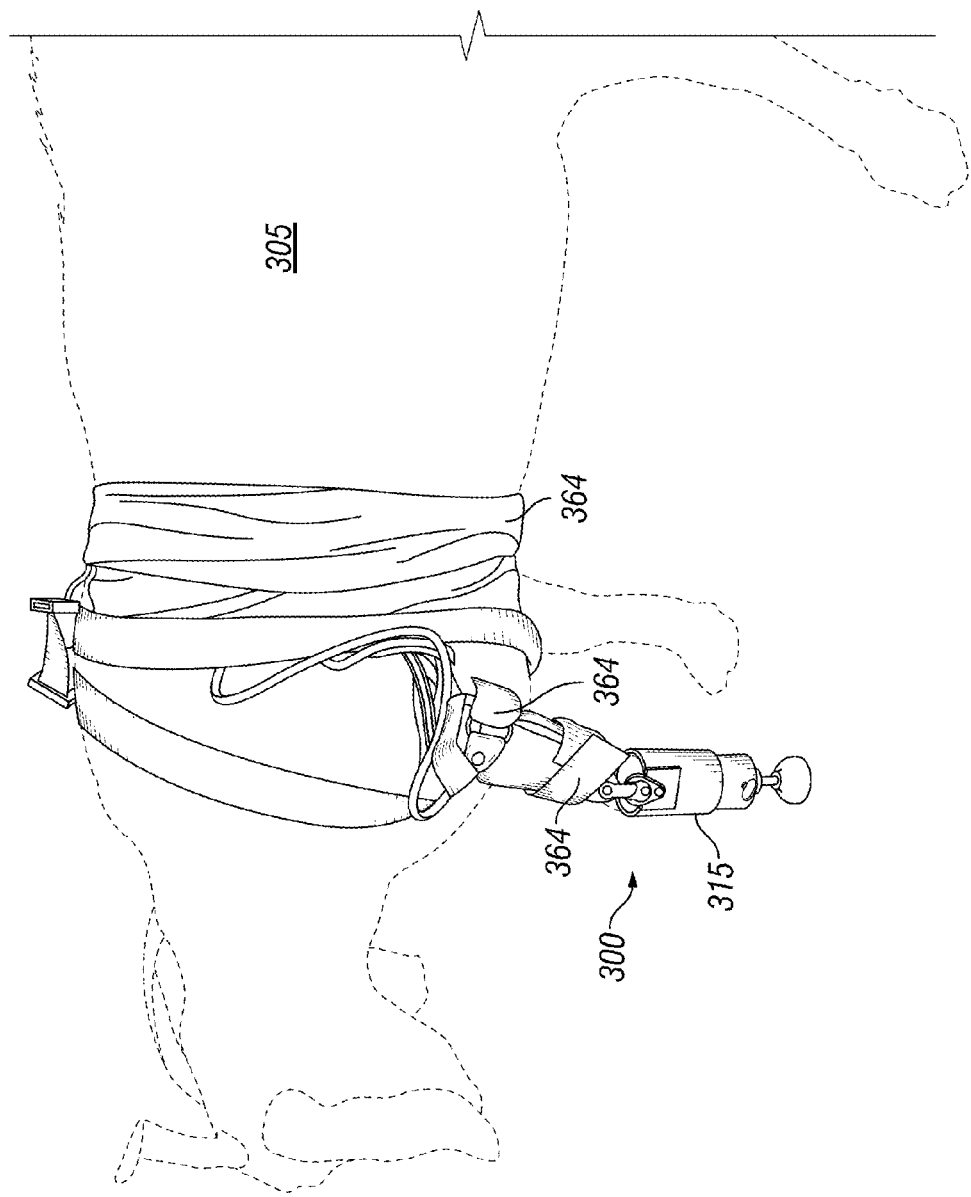

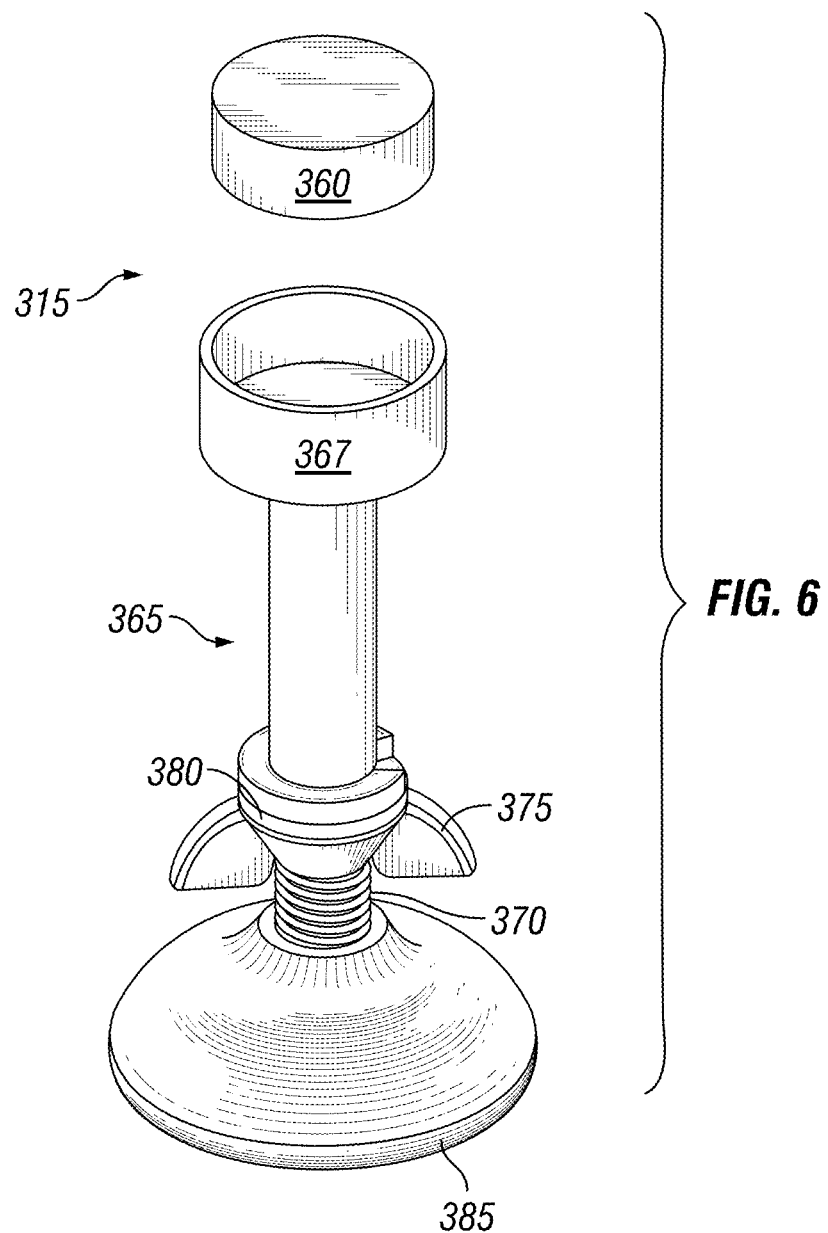

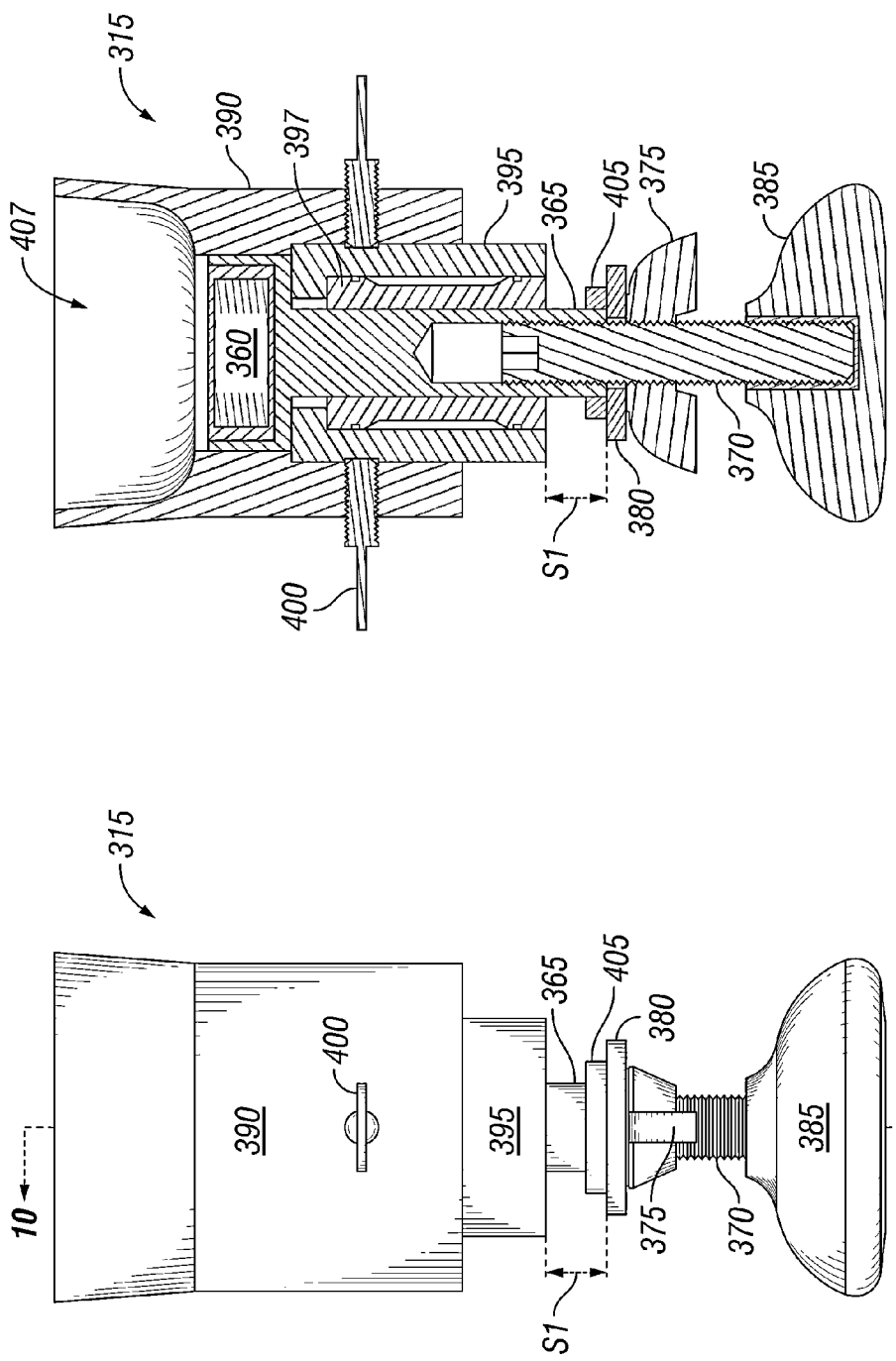

MAGNETIC PROSTHETIC IMPLANTS AND METHODS THEREOF

CROSS-REFERENCE TO RELATED APPLICATION

This United States Non-Provisional Patent Application claims the benefit, and priority, of prior filed U.S. Provisional Patent Application No. 61/503,571, filed on Jun. 30, 2011 the entire contents of which is hereby incorporated in full.

FIELD OF THE INVENTION

This disclosure relates generally to prosthetic devices. In particular, this disclosure relates to prosthetic devices having internal magnetic forces and methods thereof.

BACKGROUND OF THE INVENTION

With reference to FIG. 1, an example of a prior prosthetic device 100 is illustrated. The illustrative prior prosthetic device 100 includes a prosthetic 105 affixed, via a socket connector 110, to a prosthetic socket 115. The prosthetic socket 115 may have been a "sleeve" or "jacket" into which the residual limb 120 (having a bone 125) may have been affixed through suitable connections such as compressive vacuum, suction, straps, elastic band, and the like (not shown). Optionally, a gel liner 130 may have been used to aid in comfort and/or fit.

With reference to FIG. 2, an example of an alternative prior prosthetic device 200 is illustrated. The alternative prior prosthetic device 200 includes a female implant 205 surgically implanted into a bone 210 of a residual limb 215. A connecting screw 220 is screwed into the female implant 205 through an abutment piece 225, which protrudes through the skin of the residual limb 215. A torque absorber 230 may have been affixed to the connecting screw 220. The torque absorber 230 received a component connector 235 to which could be affixed a prosthetic 240.

SUMMARY OF THE INVENTION

Various illustrative embodiments of the present disclosure provide a prosthetic implant device and related methods are provided. In accordance with one aspect of an illustrative embodiment of the present disclosure, the prosthetic device may include an internal component and an external component. The internal component may have an implant portion associated with one or more rare earth magnets. The internal component may be of a size and shape suitable for surgical implantation into the residual limb of the amputee. The implant portion may be of a size and shape suitable for surgical implantation into a bone within the residual limb of the amputee. The one or more rare earth magnets may generate at least one magnetic field. The external component may have a prosthetic connection associated with a magnetic element. The magnet element may be in adaptable magnetic association with the at least one magnetic field generated by the one or more rare earth magnets.

In accordance with an alternative illustrative embodiment of the present disclosure, various methods are provided. An illustrative method may include implanting an internal component of a prosthetic implant device into a residual limb of an amputee. The internal component may have an implant portion associated with one or more rare earth magnets. The internal component may be of a size and shape suitable for surgical implantation into the residual limb of the amputee. The implant portion may be of a size and shape suitable for surgical implantation into a bone within the residual limb of the amputee. The one or more rare earth magnets may generate at least one magnetic field. The method may include disposing an external component of the prosthetic implant device in magnetic association with the internal component. The external component may have a prosthetic connection associated with a magnetic element. The magnet element may be in adaptable magnetic association with the at least one magnetic field generated by the one or more rare earth magnets.

BRIEF DESCRIPTION OF THE DRAWING

The present prosthetic apparatus may be understood by reference to the following description taken in conjunction with the accompanying drawing figures, which are not to scale and contain certain aspects in exaggerated or schematic form in the interest of clarity and conciseness, wherein the same reference numerals are used throughout this description and in the drawings for components having the same structure, and primed reference numerals, if any, are used for components having a similar function and/or construction to those elements bearing the same unprimed reference numerals, and wherein:

FIG. 1 is an illustrative embodiment of a prior prosthetic device;

FIG. 2 is an exploded view of an illustrative embodiment of an alternative prior prosthetic device;

FIG. 3 is a perspective view of an amputated goat having a prosthetic implant device of the present disclosure;

FIG. 6 is a perspective view of an embodiment of an external component of a prosthetic implant device of the present disclosure, with a prosthetic connection;

FIG. 9 is a side view of a second alternative embodiment of an external component of a prosthetic implant device of the present disclosure in an unloaded condition;

FIG. 10 is a cross-sectional view of the external component of FIG. 9 taken along cut line 10-10;

DETAILED DESCRIPTION OF THE INVENTION

Figure 4A:
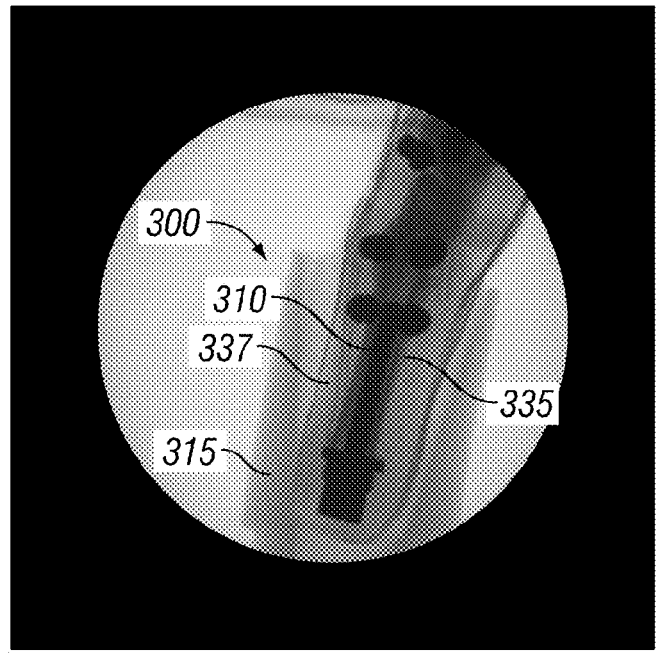
FIG. 4A is an x-ray view of an embodiment of an internal component of a prosthetic implant device of the present disclosure surgically implanted into a medullary canal of a goat.

Detailed embodiments of the present prosthetic implant device, system, and methods are disclosed herein; however, it is to be understood that the disclosed embodiments are merely illustrative of the prosthetic implant device, system, and methods that may be embodied in various forms. In addition, each of the examples given in connection with the various embodiments of the systems and methods are intended to be illustrative, and not restrictive. Further, the drawing figures and photographs above and below are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present prosthetic implant device, system, and methods.

Figure 4B:
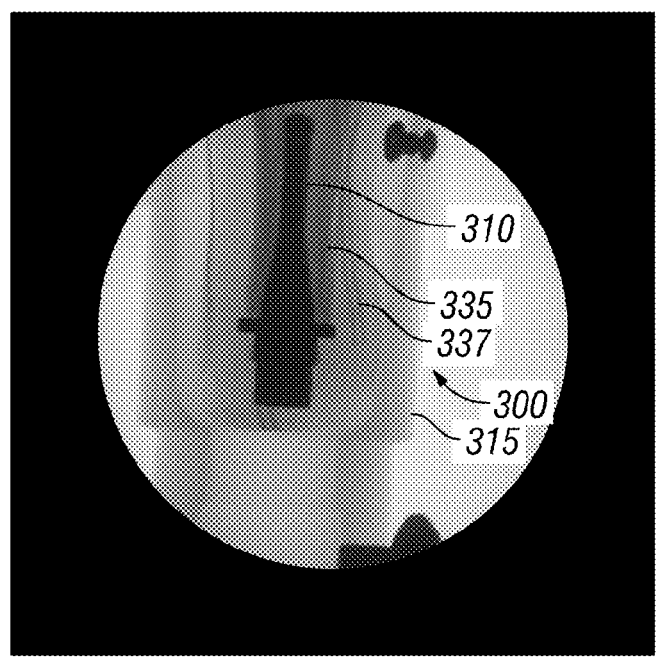
FIG. 4B is a second x-ray view of an embodiment of an internal component of a prosthetic implant device of the present disclosure surgically implanted into a medullary canal of a goat.

With reference to FIGS. 3, 4A, and 4B, an embodiment of a prosthetic implant device 300 of the present disclosure is illustrated. The prosthetic implant device 300 is illustrated as engaged with an amputated leg (otherwise referred to herein as a residual limb 337) of a goat 305. The prosthetic implant device 300 may include an internal component 310 and an external component 315. The illustrative embodiment of FIG. 3 is non-limiting and prosthetic implant devices within the scope of this disclosure may be modified such that the prosthetic implant devices may be used within any amputated limb, including for example a leg or arm, of any animal, including without limitation goats, cows, bulls, horses, dogs, cats, birds, and primates including humans.

Figure 5:
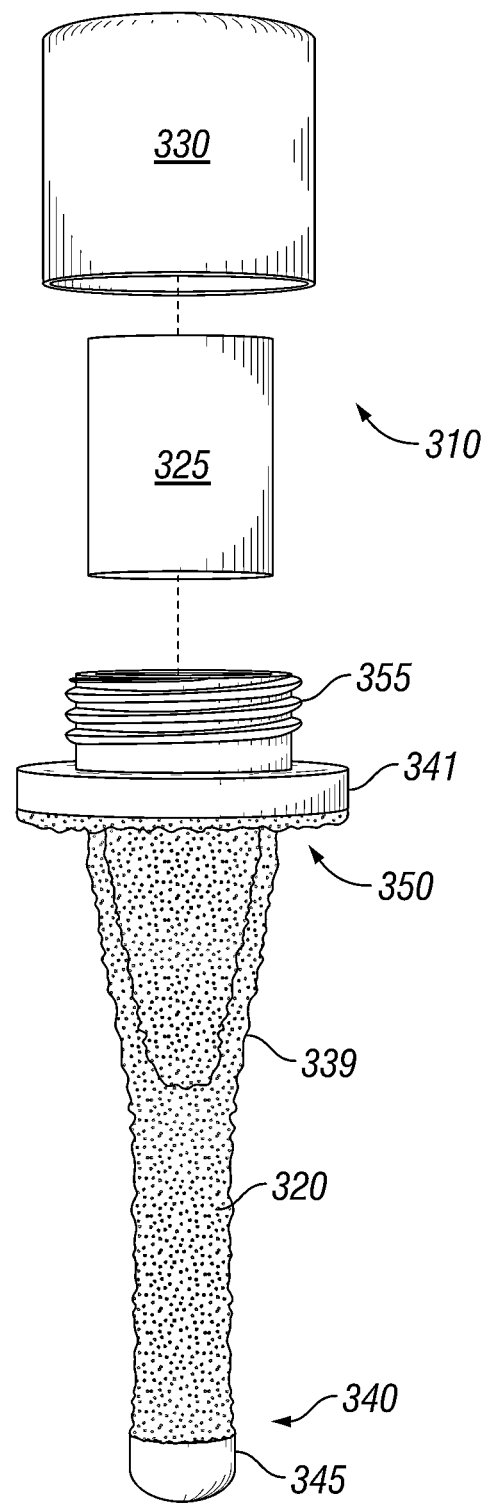
FIG. 5 is an exploded view of an embodiment of an internal component of a prosthetic implant device of the present disclosure.
Figure 8:
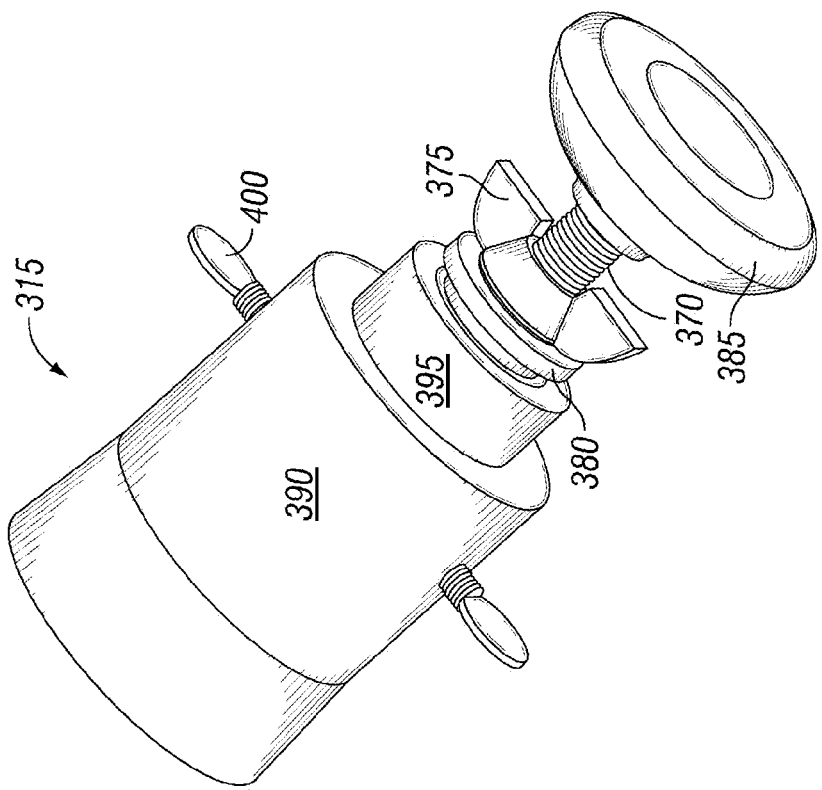
FIG. 8 is a perspective view of an alternative embodiment of the external component of FIG. 7 in a loaded condition.
Figure 7:
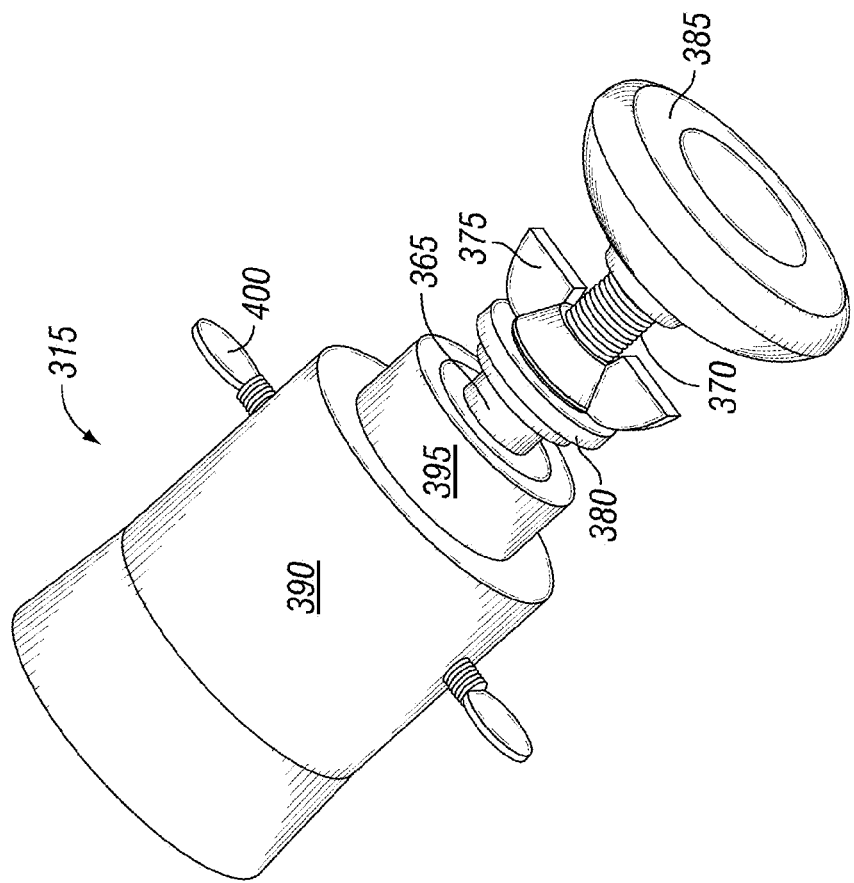
FIG. 7 is a perspective view of an alternative embodiment of an external component of a prosthetic implant device of the present disclosure in an unloaded condition.

An embodiment of the internal component 310 is illustrated with reference to FIGS. 4A, 4B and 5. The internal component 310 may include at least an implant portion 320, one or more magnets 325, and an optional magnet housing 330 (present, but not visible in the x-rays of FIGS. 4A and 4B). In an embodiment, the implant portion 320 may be of a size and shape suitable to be surgically fixed to, about, or within a patient's bone or skeleton 335 of a residual limb 337. In an embodiment, the implant portion 320 may be of a size and shape suitable to form a friction fit within a surgically prepared hole, or cavity, within residual bone of an amputee's (or patient's) residual limb 337. In further embodiments, the implant portion 320 may include grooves (not shown) or biting ridges (not shown) which may be "screwed into" or otherwise engaged with a surgically prepared hole, or cavity, within the residual bone of an amputee's (or patient's) residual limb 337.

In still further embodiments, the implant portion 320 may be manufactured from a variety of suitable materials, including those having the requisite strength and biocompatibility characteristics to function as the implant portion 320, including but not limited to any of the following, individually or in combination, graphite, pyrocarbon, ceramic, aluminum oxide, silicone nitride, silicone carbide or zirconium oxide; metal and metal alloys, e.g., Co—Cr—W—Ni, Co—Cr—Mo, CoCr alloys, CoCr molybdenum alloys, Cr—Ni—Mn alloys; powder metal alloys, 316L or other stainless steels, Ti and Ti alloys including Ti 6A1-4V ELI; polymers, e.g., polyurethane, polyethylene, polypropylene, thermoplastic elastomers, polyaryletherketones such as polyetheretherketone (PEEK) or polyetherketoneketone (PEKK); biomaterials such as polycaprolactone; and diffusion hardened materials such as Ti-13-13, zirconium and niobium. Moreover, the implant portion 320 may be coated with a coating 339 of a variety of suitable materials, including any of the following, individually or in combination, porous coating systems on bone-contacting surfaces, hydrophilic coatings on load-bearing surfaces, hydroxyapatite coatings on bone-contacting surfaces, and tri-calcium phosphate on bone-contacting surfaces. Other suitable coatings may include growth factors and other biological agents such as bone morphogenetic proteins (BMP's), transforming growth factor beta, among others. In an embodiment, the outer coating of the implant portion 320 may be harder than the core of the implant portion 320. Additionally, components of the invention may be molded or cast, hand-fabricated or machined.

With reference to FIGS. 4A and 4B, the implant portion 320 is illustrated as being surgically implanted within the medullary canal 335 of a goat. The one or more magnets 325 may be formed of any magnetic material, and are preferably formed, contain, or are derived from rare earth metals, including without limitation scandium, yttrium, lanthanum, cerium, praseodymium, neodymium, promethium, samarium, samarium-cobalt, europium, gadolinium, terbium, dysprosium, holmium, erbium, thulium, ytterbium, lutetium, and combinations thereof such as for example, and without limitation, neodymium-iron-boron (Nd—Fe—B), samarium cobalt (Sm—Co), samarium iron nitride (Sm—Fe—N), cerium-cobalt permanent magnets ($Ce(CuCo)_5$), as well as other permanent magnets or magnetic materials including, without limitation, alnico alloys (Al—Ni—Co V), platinum-cobalt alloys (Pt—Co), iron based alloys such as iron-cobalt (FeCo), iron-platinum (FePt), hard ferrites such as Barium ferrite ($BaFe_{12}O_{19}$) or Strontium ferrite ($SrFe_{12}O_{19}$), magnetic shape memory alloys such as (Ni—Mn—Ga), manganese-bismuth permanent magnets (MnBi), and Cobalt-nickel-chromium alloys (Co—Ni—Cr). The housing 330 (shown in FIG. 5) may be formed of any material include plastics such as polyether ether ketone ("PEEK"), ceramics, and metals. In an embodiment, the housing 330 may function as a physical barrier between the one or more magnets 325 and the limb or bone of the amputee so as to prevent physical contact with the magnets 325, which may not be bio-compatible, while at the same time presenting a minimum amount of interference with the magnetic field generated by the one or more magnets 325. In an embodiment, the entirety of the implant portion 320 may be implanted within the residual limb 337 of a patient or amputee. In this manner, the implant portion 320, the one or more magnets 325, as well as the optional housing 330, may be completely disposed inside of the residual limb 337 and not visible without the aid of an x-ray or the like machine. Applied to the one or more magnets 325 may be one or more coatings or surface treatments 339, which Applicant presently believes may increase the biocompatibility of the one or more magnets 325 with the residual limb. Suitable coatings or surface treatments 339—which may be applied by any of a variety of applications such as spraying, painting, and the like to any of a variety of thicknesses generally ranging from about 100 nanometers to about 1 millimeter—may include, without limitation, nickel plating (nickel-copper-nickel), gold, titanium, titanium nitride, chromium nitride, palladium, stainless steel, polytetrafluoroethylene (often sold under the DuPont trademark Teflon™), and the like. Thus, the internal component 310 may be entirely sub-dermal, and Applicant presently believes the internal component 310 may be inserted in a single surgery; optionally, during the original amputation surgery. Without wishing to be bound by the theory, Applicant presently believes that the risk to outside infection may be eliminated (or otherwise reduced) because there are no or minor transcutaneous elements to attract contaminants.

In further embodiments, the implant portion 320 may include additional features and/or modifications to enhance its fit within the residual limb 337. For example, a first end 340 of the implant portion 320 may be capped with a metal, plastic, or ceramic cap 345 and a second end 350 of the implant portion 320 may blend, flare, or otherwise be integral with a shoulder 341. The shoulder 341—as with the entirety of the disclosed prosthetic implant device 300 and its component elements—may be of any size and shape depending on the particular limb and animal it is being designed to engage. In the embodiment with respect to FIGS. 4A, 4B, and 5, the shoulder 341 may be of a general cylindrical disk shape. The second end 350 of the implant portion 320 may further include connections such as threads 355, snaps, tabs, and the like suitable for receiving, engaging, and otherwise connecting the housing 330—disposed within are the one or more magnets 325—with the implant portion 320. In this embodiment, the housing 330 may include connections (not shown) for reciprocating engagement or connection with the implant portion 320. In an embodiment, within the housing 330 may be an array of one or more magnets 325.

With reference to FIGS. 6-12, an illustrative embodiment of an external component 315 is provided. The external component 315 may include a magnetic element 360 affixed to, connected to, or otherwise engaged with, a shaft 365. In an embodiment, the magnetic element 360 may be integrally formed with the shaft 365 (not shown). In an embodiment, the magnetic element 360 may be a separate piece from the shaft 365, and may be sized to be received by or with a flat piece, a cup, or a container 367 that is affixed to, connected to, integrally formed with, or otherwise engaged with the shaft 365. The magnetic element 360 (which may be a magnet itself) may be of a size and magnetic strength to engage the one or more magnets 325 (and more precisely, the one or more magnetic fields generated from the one or more magnets 325) of the internal component 305 of the prosthetic implant device 300. The magnetic element 360 may react against (or repel), or react to pull toward (or attract), the one or more magnetic fields (not shown) created by the one or more magnets 325. Generally, without limitation, Applicant presently believes that prosthetic implant devices 300 of the present disclosure utilized in residual limbs (not shown) which experience more forces pulling them away from the body than against the body, such as human arms, will include magnetic elements 360 that react to pull (or attract) the one or more magnetic fields (not shown) created by the one or more magnets 325. Generally, without limitation, Applicant presently believes that prosthetic implant devices of the present disclosure utilized in residual limbs 337 which experience more forces pushing them against or toward the body than away from the body, such as human legs, will include magnetic elements 360 that react against (or repel) the one or more magnetic fields (not shown) created by the one or more magnets 325.

In further embodiments, the external component 315 may include additional features and/or modifications to enhance its engagement, or association, with the residual limb 337 (illustrated in FIGS. 4A and 4B). For example, (illustrated in FIG. 3) straps, buckles, and the like 364 may be used to facilitate the association with, or to further secure and/or align, the external portion 315 to the amputated limb or body of the amputee 305. Continuing with reference to FIGS. 6-12, the external portion 315 may include a post 370 associated with or otherwise secured to the shaft 365. In an embodiment, the post 370 may include grooves or ridges or threads and may be screwed into a bore of the shaft 365 having reciprocal grooves or ridges or threads. The length of the post 370, which may protrude from the shaft 365, may be adjusted by an adjustment device such as without limitation a wing nut 375. A washer 380 may further facilitate the engagement of the post 370 and shaft 365, as well as the adjustability of the post 370 by the wing nut 375. The post 370 may be further associated with an end prosthetic 385. The end prosthetic 385 may be in the form of a foot, pad, claw, hoof, hand, hook, stub, post, and the like.

Continuing with reference to FIGS. 7-12, a prosthetic connection (also called a prosthetic socket or prosthetic sleeve) 390 may be associated with, engaged with, or disposed about the magnetic element 360 and at least a portion of the shaft 365. The prosthetic socket 390 may be of a size and shape suitable for housing the residual limb of the amputee. The prosthetic socket 390 may further house, contain, or otherwise be associated with a bushing 395, which may be optionally cylindrical or tubular in shape. In an embodiment, the bushing 395 may provide a channel through which the shaft 365 may be disposed. The bushing 395 may further include, or be associated with, a linear bearing 397 or the like, that may provide a channel, or bore, through which the shaft 365 may be disposed. One or more pins, anchors, or screws 400 may be disposed through a portion of the prosthetic socket 390 to provide mechanical association between the prosthetic socket 390 and the bushing 395.

The external component 315 is illustrated in an embodiment of an unloaded configuration with reference to FIGS. 9 and 10. In the unloaded configuration the magnetic element 360 is in its lowest position relative to the prosthetic socket 390, and there is a first space, or clearance, S1, between the end of the bushing 395, or linear bearing 397, and the washer 380. The linear bearing 397 may be press fit, or otherwise secured with pins, anchors, or screws (not shown) into the bushing 395. In an embodiment, one or more shims 405 may be disposed between the end of the bushing 395 and the end prosthetic 385, which may optionally function as a stop for the magnetic element 360, or the container 367 optionally formed integral with the shaft 365; alternatively one or more shims 405 are disposed between the end of the bushing 395 or linear bearing 397 and the washer 380. In an embodiment, the residual limb 337 having the internal component 310 (not shown in FIGS. 9 and 10) may be associated with or disposed within an opening 407 of the prosthetic socket 390 of the external component 315.

Figure 12:
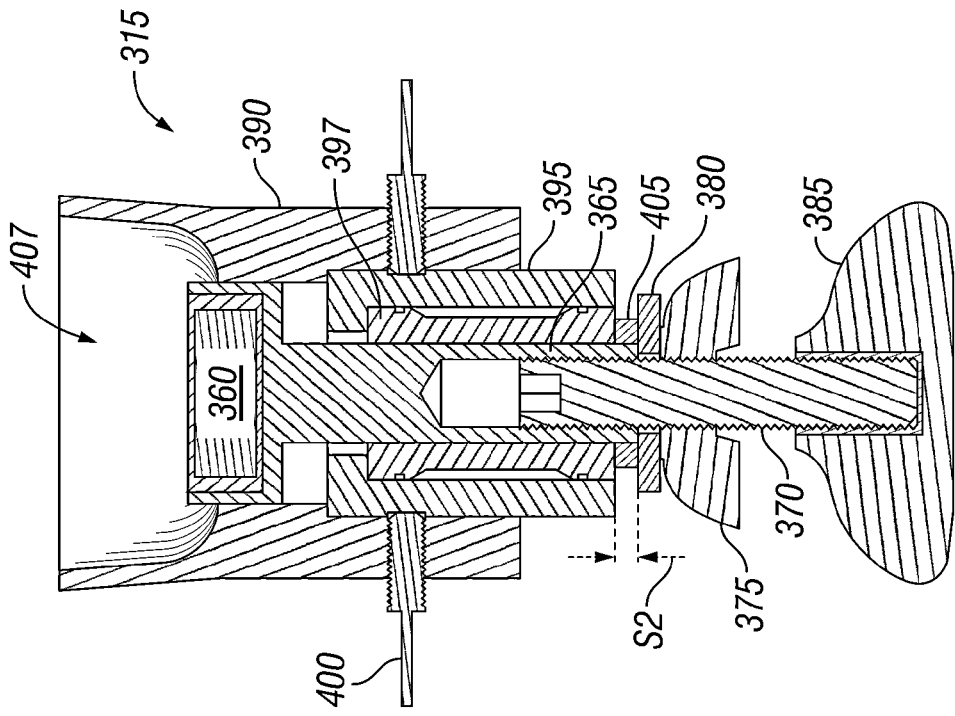
FIG. 12 is a cross-sectional view of the external component of FIG. 11 taken along cut line 12-12.
Figure 11:
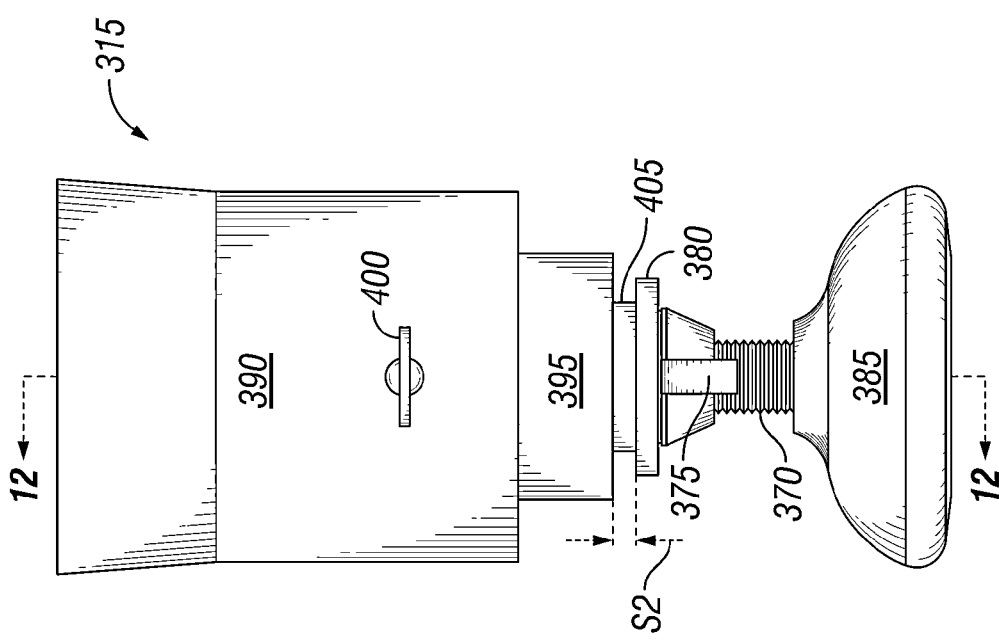
FIG. 11 is a side view of the external component of FIG. 9 in a loaded condition.

The external component 315 is illustrated in an embodiment of a loaded configuration with reference to FIGS. 11 and 12. In the loaded configuration the magnetic element 360 may be in a position higher relative to the lowest position described above, and there may be a second space S2, between the end of the bushing 395 and the washer 380. In an embodiment, the second space S2 is near zero, or zero, and the end of the bushing 395 and the washer 380 are touching or otherwise engaged. In an embodiment, one or more shims 405 are disposed between the end of the bushing 395 and the end prosthetic 385; alternatively one or more shims 405 are disposed between the end of the bushing 395 and the washer 380. In an embodiment of the loaded configuration, the end of the bushing 395 is touching or otherwise engaged with at least one shim 405. In an embodiment, additional shims 405 may be stacked on top of one another in order to facilitate adjustment of the proximity of the internal component 310 and the external magnetic element 360.

In various embodiments, methods of affixing a prosthetic implant device 300 to a residual limb 337 of an amputee 305, including without limitation a dog, cat, cow, bull, horse, goat, sheep, non-human primates, and human are provided herein. In an embodiment, the amputee 305 may initially be a patient who, for a host of reasons, may require amputation of one or more limbs. The patient may receive amputation of at least one limb. An internal component 310 (as disclosed herein above and below) may be surgically implanted into the residual limb of the patient. In an embodiment, the patient may receive surgical implantation of the internal component 310 immediately after receiving amputation surgery and before the patient regains consciousness from anaesthesia. Alternatively, the patient may receive amputation (either by surgery or injury) and later receive surgical implantation of the internal component 310. The residual limb of the patient, containing the internal component 310, may be mated, aligned, introduced, or otherwise engaged with an opening 407 of a prosthetic connection 390 of an external component 315 having a magnetic element 360. Connections such as straps, buckles, and the like may assist to affix or associate the residual limb 337 with the external component 315.

Continuing with the method, in an embodiment, the external component 315 may be loaded when the amputee moves the residual limb 337 (containing or housing the internal component 310) toward or away from the external component 315. In an embodiment, the amputee may move the residual limb 337 (containing or housing the internal component 310) toward the external component 315, and may thereby force the prosthetic socket 390 down the shaft 365 until the magnetic field of the one or more magnets 325 of the internal component 310 repels against the magnetic element 360 of the external component 315. Applicant presently believes that the repulsion between the magnetic field of the one or more magnets 325 of the internal component 310 and the magnetic element 360 of the external component 315 may reduce the relative compressive force experienced by the soft tissues of the residual limb during loading (i.e., during walking) and instead transfer the force, or at least a portion of the force directly, to the bone or skeletal system to which the internal component 310 is associated or engaged. Applicant presently further believes that in addition to eliminating or reducing the contact forces between the residual stump soft tissues and the prosthetic socket 390, the magnetic repulsion between the magnetic element 360 and the magnets 325 of the internal component 310 may serve as a shock absorber when used for a lower extremity. In an embodiment, the repulsion between the magnetic element 360 and the magnets 325 of the internal component 310 may reduce the contact pressures between the residual limb and the prosthetic device 100 (optionally the external component 315, and optionally the prosthetic socket 390, of the prosthetic device 100) by at least 10%, alternatively at least 20%, alternatively at least 30%, alternatively at least 40%, alternatively at least about 50%, alternatively at least about 60%, and alternatively at least about 70%, as compared to prior prosthetic systems having either no magnetic interaction or inferior magnetic interaction as compared to the systems disclosed herein. In an embodiment, the contact pressures between the residual limb and the prosthetic device 100 (optionally the external component 315, and optionally the prosthetic socket 390, of the prosthetic device 100) are approximately equal to, or at most about 100% (alternatively at most about 90%, 80%, 70%, 60%, or 50%) less than, the applied force imparted by the amputee. In an embodiment, the magnetic repulsion between the magnetic element 360 and the magnets 325 of the internal component 310 is approximately equal to the applied force imparted by the amputee. In an embodiment, the contact pressure is about zero.

For an upper extremity amputee, the attractive force may eliminate or reduce the need for belts and straps to aid socket stability. In an embodiment, the attractive force between the magnetic element 360 and the magnets 325 of the internal component 310 may reduce the stresses and/or strains between the residual limb and the prosthetic device 100 (optionally the external component 315, and optionally the prosthetic socket 390, of the prosthetic device 100) by at least 10%, alternatively at least 20%, alternatively at least 30%, alternatively at least 40%, alternatively at least about 50%, alternatively at least about 60%, and alternatively at least about 70% as compared to prior prosthetic systems having either no magnetic interaction or inferior magnetic interaction as compared to the systems disclosed herein.

Examples/Experiments

Three female Spanish Boer Cross goats (*Capra aegagrus hircus*), each being 5 years of age and of similar size (59-63 kg, mean 62 kg), were used in the experiment as described hereinafter. Surgical and animal care procedures were performed in accordance with federal requirements (Animal Welfare Act) following IACUC review/approval.

The animals each underwent unilateral amputation of the forelimb at mid-metacarpal. A titanium alloy implant, with commercially pure titanium spray coating and hydroxyapatite coating was inserted into the medullary canal of each animal's amputated forelimb. A PEEK housing was threaded to a distal implant end, and hermetically sealed a nickel-plated (Ni—Cu—Ni), gold-coated neodymium (NdFeB) N52-grade magnet (1.27 cm diameter, 1.59 cm height) from tissue contact.

Anatomical measurements and cast moldings of the residual limb were used to construct an external component. An externally placed magnet or non-magnet control material was used in the magnetic element of the external components in order to assess the effects, if any, of magnetic force repulsion. Dynamic contact pressures (SensorSpot™, SensorTech Corp., Greenville, S.C.) were collected at multiple limb-socket locations, including the external magnet-limb interface, during a series of externally applied loads. X-rays of one goat having the prosthetic implant device are illustrated with respect to FIGS. 4A and 4B.

The surgical implantations of the prosthetic implant device in each animal were "uneventful," i.e., each animal recovered from the initial amputation surgery and were then fitted with external components. One goat was utilized to obtain dynamic contact pressure measurements within the prosthetic implant device within the scope of the present disclosure. With an externally-applied load of approximately 6 to 10 pounds of force through the end of the prosthetic limb, contact pressures at the distal end of the stump were maximum at 17-25 pounds per square inch using an aluminium metal non-magnetic control. With the externally placed NdFeB magnet in the prosthetic, repulsive forces against the internally implanted magnet resisted the load application and reduced the contact pressures at the distal end by 40%-50%, between 8 and 15 psi, compared to control.

Figure 13:
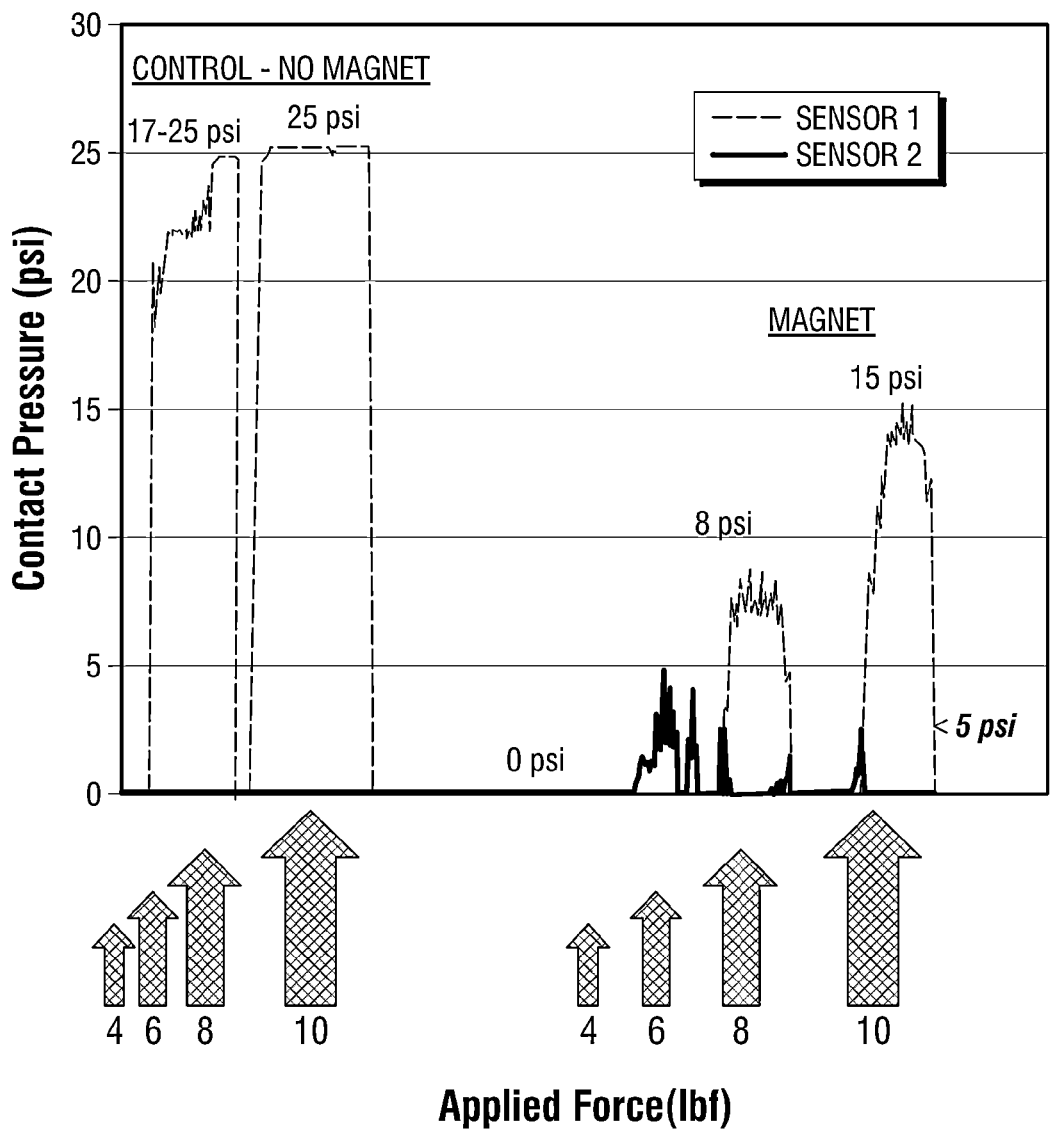
FIG. 13 is a graph illustrating contact pressure (psi) versus applied force (lbf) results of experiments that are described below.

FIG. 13 illustrates the results of the magnetic repulsive forces to reduce contact pressures at the end of the stump (sensor 1) and shift contact to the anterior socket (sensor 2) compared to control with an increasing externally applied manual load (0-10 lbf) to limb (arrows). Thus, Applicant presently believes that the prosthetic implant device of the present disclosure provides a stable, secure limb attachment, which permits greater force transmission to the skeletal structure of the amputee while minimizing soft tissue breakdown, ulcer formation, and infection, and without requiring—or otherwise minimizing the need for—permanent skin penetration.

Without wishing to be bound by the theory, in the present method and implants, the loads are transferred from a prosthesis to the skeleton, without the need for permanent skin penetrations. The implant may be embedded within the residual limb, and may react with the prosthetic socket to provide a stable, non-contact connection between the patient and the prosthesis.

We claim:

1. A prosthetic implant device comprising:
   an internal component comprising an implant portion and one or more rare earth magnets, the internal component being of a size and shape suitable for surgical implantation into a residual limb of an amputee, the implant portion being of a size and shape suitable for surgical implantation into a bone within the residual limb of the amputee, the one or more rare earth magnets generating at least one magnetic field; and
   an external component comprising a prosthetic connection, a magnetic element connected to a shaft, and a linear bearing connected to the prosthetic connection and through which the shaft is disposed, wherein the linear bearing permits:
   (a) (i) the prosthetic connection and (ii) the shaft and the magnetic element, to move relative to one another in response to loading, wherein and
   (b) the magnetic element to be in adaptable magnetic association with the at least one magnetic field generated by the one or more rare earth magnets of the internal component in response to loading.

2. The implant of claim 1, wherein the one or more rare earth magnets include at least one rare earth metal selected from the group consisting of: scandium, yttrium, lanthanum, cerium, praseodymium, neodymium, promethium, samarium, samarium-cobalt, europium, gadolinium, terbium, dysprosium, holmium, erbium, thulium, ytterbium, lutetium, and combinations thereof.

3. The implant of claim 1, wherein the at least one rare earth magnets is a nickel-plated (Ni—Cu—Ni), gold-coated neodymium (NdFeB) N52-grade magnet.

4. The implant of claim 3, wherein the at least one rare earth magnet is generally cylindrical having a diameter ranging from about 1 centimeter to about 5 centimeters, and a height ranging from about of about 1 centimeter to about 5 centimeters.

5. The implant of claim 3, wherein the rare earth magnets comprise an array of gold-coated neodymium (NdFeB) N52-grade magnets.

6. The implant of claim 1, wherein the internal component is designed to be entirely sub-dermal and the external component is designed to be entirely outside of the residual limb of the amputee.

7. The implant of claim 1, wherein the implant portion is of a size and shape suitable for surgical implantation into a bone within a leg or arm of a dog, cat, cow, bull, horse, goat, sheep, non-human primate, or human.

* * * * *